US011896650B2

(12) United States Patent
Albanese et al.

(10) Patent No.: US 11,896,650 B2
(45) Date of Patent: *Feb. 13, 2024

(54) ENHANCING CHEMOTHERAPY IN MEDULLOBLASTOMA AND GLIOBLASTOMA WITH HIGH BASAL P53 LEVELS

(71) Applicant: GEORGETOWN UNIVERSITY, Washington, DC (US)

(72) Inventors: Christopher Albanese, Pelham, NY (US); Aisha Naeem, Springfield, VA (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/656,365

(22) Filed: Mar. 24, 2022

(65) Prior Publication Data

US 2022/0241379 A1  Aug. 4, 2022

Related U.S. Application Data

(63) Continuation of application No. 16/979,817, filed as application No. PCT/US2019/021797 on Mar. 12, 2019, now Pat. No. 11,311,606.

(60) Provisional application No. 62/642,334, filed on Mar. 13, 2018.

(51) Int. Cl.
*A61K 38/00* (2006.01)
*A61K 38/22* (2006.01)
*A61P 35/00* (2006.01)
*A61K 31/475* (2006.01)
*A61K 31/704* (2006.01)

(52) U.S. Cl.
CPC ........ *A61K 38/2292* (2013.01); *A61K 31/475* (2013.01); *A61K 31/704* (2013.01); *A61P 35/00* (2018.01)

(58) Field of Classification Search
CPC .............. A61K 2300/00; A61K 31/475; A61K 31/704; A61K 33/243; A61K 38/2292; A61K 45/06; A61P 35/00; A61P 25/00; C07K 14/4746
See application file for complete search history.

(56) References Cited

U.S. PATENT DOCUMENTS

2015/0148390 A1  5/2015  Scheffler et al.

FOREIGN PATENT DOCUMENTS

WO  WO2003027285 A1 *  4/2003

OTHER PUBLICATIONS

Liang et al. (Aging and Disease 8:850-867, 2017). The Effects of Baicalin and Baicalein on Cerebral Ischemia: A Review (Year: 2017).*
Gessi et al. J Neurooncol (2012) 106:135-141. p53 expression predicts dismal outcome for medulloblastoma patients with metastatic disease (Year: 2012).*
Dhillon Sohita BioDrugs (2013) 27:375-392. Bevacizumab Combination Therapy: A Review of its Use in Patients with Epithelial Ovarian, Fallopian Tube, or Primary Peritoneal Cancer (Year: 2013).*
Gao et al. Med Chem Res. Aug. 2016 ; 25(8): 1515-1523. Anticancer properties of baicalein: a review (Year: 2016).*
Pastwa et al. (The InterN. J. of Biochem. & Cell Biol. 53 (2014) 423-431). Wortmannin potentiates the combined effect of etoposide and cisplatin in human glioma cells. (Year: 2014).*
Morris et al. Thymosin β4 improves functional neurological outcome in a rat model of embolic stroke. Neuroscience. Aug. 25, 2010; 169(2): 674-682. (Year: 2010).*
U.S. Appl. No. 16/979,817 , "Non-Final Office Action", dated Jul. 30, 2021, 11 pages.
U.S. Appl. No. 16/979,817 , "Notice of Allowance", dated Dec. 23, 2021, 7 pages.
Albanese et al., "Models of Prostate Cancer", Drug Discovery Today: Disease Models, vol. 2, No. 1, 2005, pp. 7-13.
Albanese et al., "Preclinical Magnetic Resonance Imaging and Systems Biology in Cancer Research: Current Applications and Challenges", The American Journal of Pathology, vol. 182, No. 2, 2013, pp. 312-318.
Beauchamp et al., "Arsenic Trioxide Inhibits Human Cancer Cell Growth and Tumor Development in Mice by Blocking Hedgehog/GLI Pathway", The Journal of Clinical Investigation, vol. 121, No. 1, Jan. 2011, pp. 148-160.
Buss et al., "The Wip1 Oncogene Promotes Progression and Invasion of Aggressive Medulloblastoma Variants", Oncogene, vol. 34, 2015, pp. 1126-1140.
Caccamo et al., "Necroptosis Activation in Alzheimer's Disease", Nature Neuroscience, vol. 20, No. 9, 2017, pp. 1236-1246.
Ding et al., "Combination of Baicalein and Temozolomide Eradicates Malignant Glioma Through Cell Apoptosis", International Journal of Sciences, vol. 5, No. 11, Nov. 2016, pp. 87-92.
Ho et al., "PP2A Inhibition With Lb100 Enhances Cisplatin Cytotoxicity and Overcomes Cisplatin Resistance in Medulloblastoma Cells", Oncotarget, vol. 7, No. 11, 2016, pp. 12447-12463.
Lee et al., "Divergent Brain Changes in Two Audiogenic Rat Strains: A Voxel-based Morphometry and Diffusion Tensor Imaging Comparison of the Genetically Epilepsy Prone Rat (Gepr-3) and the Wistar Audiogenic Rat (War)", Neurobiology of Disease, vol. 111, 2018, pp. 80-90.
Li et al., "Thymosin B4 Reduces Senescence of Endothelial Progenitor Cells via The PI3K/Akt/Enos Signal Transduction Pathway", Molecular Medicine Reports, vol. 7, Issue 2, Feb. 2013, pp. 598-602.

(Continued)

Primary Examiner — Aradhana Sasan
Assistant Examiner — Mercy H Sabila
(74) Attorney, Agent, or Firm — Kilpatrick Townsend & Townsend & Stockton LLP

(57) ABSTRACT

Provided herein is a method of treating medulloblastoma or glioblastoma in a subject by administering to the subject a PI3K activator (e.g., thymosin β-4 or a derivative thereof) and one or more chemotherapeutic agents and/or radiation. The combination therapy is effective in the treatment of medulloblastoma or glioblastoma characterized by cells with elevated p53 levels.

19 Claims, 12 Drawing Sheets

Specification includes a Sequence Listing.

(56) References Cited

OTHER PUBLICATIONS

Morris et al., "Thymosin B4 Improves Functional Neurological Outcome in a Rat Model of Embolic Stroke", Neuroscience, vol. 169, No. 2, 2010, pp. 1-20.
Nagpal et al., "Revisiting the Role of p53 in Primary and Secondary Glioblastomas", Anticancer Research, vol. 26, 2006, pp. 4633-4640.
International Application No. PCT/US2019/021797, "International Preliminary Report on Patentability", dated Sep. 24, 2020, 6 pages.
International Application No. PCT/US2019/021797, "International Search Report and Written Opinion", dated May 14, 2019, 9 pages.
Rodriguez et al., "A Reduction in Pten Tumor Suppressor Activity Promotes ErbB-2-Induced Mouse Prostate Adenocarcinoma Formation Through the Activation of Signaling Cascades Downstream of PDK1", The American Journal of Pathology, vol. 174, No. 6, Jun. 2009, pp. 2051-2060.
Sakamaki et al., "Cyclin D1 Determines Mitochondrial Function in Vivo", Molecular and Cellular Biology, vol. 26, No. 14, Jul. 2006, pp. 5449-5469.
Sirajuddin et al., "Quantifying the CDK Inhibitor VMY-1-103's Activity and Tissue Levels in an in Vivo Tumor Model by LC-MS/MS and by MRI", Cell Cycle, vol. 11, No. 20, 2012, pp. 3801-3809.
Sun et al., "Cell Type-Specific Dependency on the PI3K/Akt Signaling Pathway for the Endogenous EPO and VEGF Induction by Baicalein in Neurons Versus Astrocytes", PLoS One, vol. 8, Issue 7, e69019, Jul. 19, 2013, 16 pages.
Tian et al., "Integration of Network Biology and Imaging to Study Cancer Phenotypes and Responses", IEEE/ACM Transactions on Computational Biology and Bioinformatics, vol. 11, No. 6, 2014, pp. 1009-1019.
Tricoli et al., "Characterization of the Effects of Defined, Multidimensional Culture Conditions on Conditionally Reprogrammed Primary Human Prostate Cells", Oncotarget, vol. 9, No. 2, 2018, pp. 2193-2207.
Waye et al., "The P53 Tumor Suppressor Protein Protects Against Chemotherapeutic Stress and Apoptosis in Human Medulloblastoma Cells", Aging, vol. 7, No. 7, Oct. 2015, pp. 854-867.
Wirsching et al., "Thymosin B 4 Gene Silencing Decreases Stemness and Invasiveness in Glioblastoma.", Brain, vol. 137, No. 2, Dec. 18, 2013, pp. 433-448.
Xiong et al., "Neuroprotective and Neurorestorative Effects of Thymosin Beta4 Treatment Following Experimental Traumatic Brain Injury", Annals of the New York Academy of Sciences, vol. 1270, 2012, pp. 51-58.
Yanagisawa et al., "Proteomic Patterns of Tumour Subsets in Non-Small-Cell Lung Cancer", The Lancet, vol. 362, Issue 9382, Aug. 9, 2003, pp. 433-439.
Bouvier-Labit, et al., "Prognostic Significance of Ki67, p53 and Epidermal Growth Factor Receptor Immunostaining in Human Glioblastomas", Neuropathology and Applied Neurobiology, vol. 24, Oct. 1998, pp. 381-388.
Chaurasia, et al., "Immunohistochemical Analysis of ATRX, IDH1 and p53 in Glioblastoma and Their Correlations with Patient Survival", Journal of Korean Medical Science, vol. 31, No. 8, Aug. 2016, pp. 1208-1214.
Pollack, et al., "The Relationship between TPS3 Mutations and Overexpression of p53 and Prognosis in Malignant Gliomas of Childhood", Cancer Research, vol. 57, Jan. 15, 1997, pp. 304-309.
Yoon, et al., "p53 Mutation and Epidermal Growth Factor Receptor Overexpression in Glioblastoma", Journal of Korean Medical Science, vol. 16, Aug. 2001, pp. 481-488.

* cited by examiner p-value <0.05 Control plasmid vs. p110

SEQUENCE LISTING

<160> NUMBER OF SEQ ID NOS: 1

<210> SEQ ID NO 1
<211> LENGTH: 44
<212> TYPE: PRT

```
<213> ORGANISM: Homo sapiens

<400> SEQUENCE: 1

Met Ser Asp Lys Pro Asp Met Ala Glu Ile Glu Lys Phe Asp Lys Ser
1               5                   10                  15

Lys Leu Lys Lys Thr Glu Thr Gln Glu Lys Asn Pro Leu Pro Ser Lys
            20                  25                  30

Glu Thr Ile Glu Gln Glu Lys Gln Ala Gly Glu Ser
            35                  40
```

ENHANCING CHEMOTHERAPY IN MEDULLOBLASTOMA AND GLIOBLASTOMA WITH HIGH BASAL P53 LEVELS

CROSS-REFERENCE TO RELATED APPLICATIONS

This application is a continuation of U.S. application Ser. No. 16/979,817, filed Sep. 10, 2020, which is a U.S. national phase of International Patent Application No. PCT/US2019/021797 filed on Mar. 12, 2019, which claims priority to U.S. Patent Application No. 62/642,334, filed on Mar. 13, 2018. The entire contents of each application are hereby incorporated herein by this reference.

BACKGROUND

Medulloblastomas (MB) is the most prevalent childhood brain malignancies, with approximately 25% of childhood brain tumors being MB's. The propensity of MB to spread throughout the neuraxis requires that radiotherapy be delivered to the entire brain and spine (craniospinal irradiation) immediately following surgical resection, which is then followed by a 12-month regimen of intensive multi-agent chemotherapy. While the 5-year survival rate now is approximately 80%, this course of treatment has serious downside consequences, and a majority of survivors left with serious neurocognitive deficits. For children less than 3 years of age, the craniospinal irradiation is avoided due to its destructive effects on the developing nervous system. Long-term prognosis for these children is considerably worse.

Glioblastoma (GB) is the most common type of brain cancer in adults, with an incidence rate of about 3.2 per 100,000 persons in the United States. Although rare in children, glioblastoma is a particularly aggressive cancer. Treatment typically involves surgical resection when possible, followed by both radiation and chemotherapy. Despite this aggressive treatment, GB commonly recurs and prognosis remains poor.

SUMMARY

Provided herein is a method of treating medulloblastoma or glioblastoma in a subject by administering to the subject one or more chemotherapeutic agents and a PI3K activator (e.g., thymosin $\beta$-4 or a derivative thereof), by administering to the subject radiation (e.g., cranial radiation, spinal radiation, or craniospinal radiation) and a PI3K activator, and by administering to the subject one or more chemotherapeutic agents, radiation, and a PI3K activator. The combination therapy is effective in the treatment of medulloblastoma or glioblastoma characterized by cells with elevated p53 levels. In certain embodiments the PI3K activator reduces the effect of the one or more chemotherapeutic agents and/or radiation on normal cells and enhances the effect of the one or more chemotherapeutic agents and/or radiation on medulloblastoma or glioblastoma cells. The details of one or more embodiments are set forth in the description below. Other features, objects, and advantages will be apparent from the description and from the claims.

BRIEF DESCRIPTION OF THE DRAWINGS

FIG. 2A and FIG. 2B are bar graphs showing the proportion of cells undergoing apoptotic cell death as a result of infection with p53 shRNA, control pLKO, mTOR and both p53 and mTOR lentivirus in D556 cells treated for 18 hrs with DMSO, VMY (30 uM) or doxorubicin (1 uM) as assessed using Trypan blue (FIG. 2A) and annexin V and propidium iodide (PI) staining (FIG. 2B) and measured by flow cytometry. Data are shown as percent change in staining versus pLKO-control infected cells. FIG. 2C shows an immunoblot performed for the proteins shown. $\beta$-actin was used as a loading control.

FIG. 4C shows a dose response curve for D556 cells treated with Vincristine alone or Vincristine plus T$\beta$-4 using a cell proliferation assay kit wst-1. GADPH expression was used as a control.

DETAILED DESCRIPTION

Figure 1:
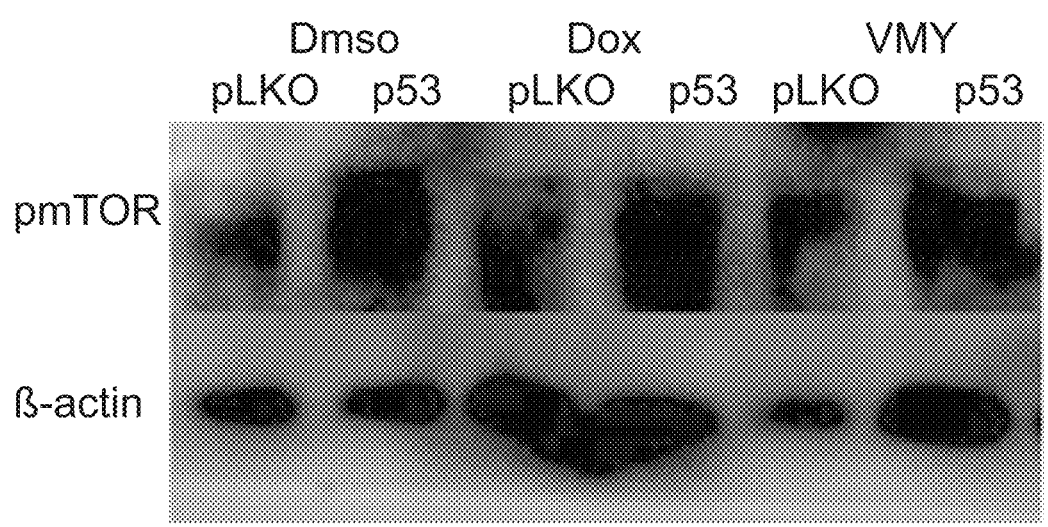
FIG. 1 shows a Western blot indicating induction of pmTOR upon p53 inhibition in D556 cells.

In MB cells with elevated p53 (e.g., D556 (wild type p53) and DAOY (mutant p53)), chemical and genetic silencing of p53 significantly enhanced chemosensitivity and resulted in the more classical chemo-suppressive effect observed in MB cell lines with much lower levels of wild type p53 (e.g., D283 cells). Transcriptomic profiling of p53-suppressed D556 cells revealed that enhanced chemosensitivity was associated with the activation of mTOR and PI3K, among other genes. shRNA knockdown of mTOR rescued the D556 cells from the effects of p53 loss, restoring chemoresistance to vincristine and doxorubicin. Conversely, the overexpression of p110$\alpha$ to induce PI3-kinase-dependent signaling, resulted in a twofold increase in drug sensitivity in D556 cells, while D283 cells were approximately twofold more chemoresistant. Nonetheless, inhibiting p53 expression or function was not previously a feasible approach to MB treatment due to the intrinsically important role p53 plays in normal cell and tissue function.

The present disclosure provides a PI3K activator that sensitizes MB or GB cells with elevated p53 to chemotherapeutic agents and/or radiation. Preferably the agent either fails to sensitize cells with normal levels of p53 to chemotherapeutic agents and/or radiation or protects such cells from cell death caused by chemotherapeutics agents and/or radiation. Preferably the agent crosses the blood brain barrier. Preferably the agent promotes nervous system recovery or function.

By way of example, thymosin β-4 (Tβ-4) is a multifunctional regenerative peptide comprising the amino acid sequence MSDKPDMAEI EKFDKSKLKK TETQEKNPLP SKETIEQEKQ AGES (SEQ ID NO:1). Tβ-4 is approved by the Food and Drug Administration for use in treating epidermolysis bullosa and other and has been found to promote healing of the skin and to support neurological recovery from stroke. The present disclosure, however, relates to the novel discovery that Tβ-4 sensitizes MB cells with high p53 levels to chemotherapeutic agents (e.g., doxorubicin, vincristine, and VMY-1-103). Additionally, Tβ-4 protects D283 (p53 low) cells from the same drugs. Thus, activation of PI3K with Tβ-4 enhances the effect of chemotherapy and/or radiation on MB cells with high basal p53 expression.

Thus, provided herein is a method of treating medulloblastoma in a subject comprising administering to the subject a chemotherapeutic agent and/or radiation along with a PI3K activator (e.g., Tβ-4 or a derivative thereof). The PI3K activator is administered at a dosage that provides the desired therapeutic effect (i.e., enhances the effect of the chemotherapeutic agent and/or radiation on the MB or GB cells having elevated levels of p53, for example, by enhancing the sensitivity of the MB cells to the chemotherapeutic agent and/or radiation). One of skill in the art determines the proper dosage of the chemotherapeutic agent(s) and/or radiation and the PI3K activator based on multiple factors including the age of the subject, the severity of the disease, and the like.

As described herein p53 is a biomarker of poor overall survival and the PI3K activator (e.g., Tβ-4) is used as a chemosensitizer and/or radiation sensitizer in MB or GB cells with elevated levels of p53. As described herein, p53 protein expression and subcellular localization can be easily assessed in resected patient MB and GB samples by standard immunohistochemistry. Furthermore, chemosensitization and/or radiation sensitizer by a PI3K activator (e.g., Tβ-4) in patients with p53 expressing tumors improves survival and decrease recurrence/relapse. Additionally, concurrent use of a PI3K activator (e.g., Tβ-4) can reduce the post-treatment morbidity and sequelae by enabling the dose reduction of the one or more chemotherapeutic agents and/or the radiation. Post-treatment quality of life of MB and GB patients plays an increasingly important part in the choice of therapies. Thus the present methods are based on defining a biomarker of risk and providing treatment strategies that improve MB and GB patient survival while reducing neurotoxicity.

The PI3K activator, as used herein, can comprise the amino acid of SEQ ID NO:1 or an amino acid sequence having at least about 90% identity to SEQ ID NO:1, wherein the amino acid sequence has the desired therapeutic effect. Thus, the pI3K activator optionally comprises Tβ-4 (SEQ ID NO:1) or a modified version or derivative thereof.

Amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the polypeptide. Amino acid substitutions are typically of single residues but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final polypeptide. Substitutional variants are those in which at least one residue has been removed and a different residue inserted in its place. Such substitutions generally are made in accordance with the following Table 1 which shows conservative substitutions.

TABLE 1

Amino Acid Substitutions.

| Original Residue | Exemplary Substitutions |
| --- | --- |
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Gln, Asn |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Thus, by way of example, derivatives or modified versions of Tβ-4 useful in the methods described herein can comprise SEQ ID NO:1 with one or more conservative amino acid substitutions, SEQ ID NO:1 with truncation of one or more amino acids from either the N- or C-termini, and/or SEQ ID NO:1 in a chimeric polypeptide. Such modifications and derivatives include, for example, SEQ ID NO:1 with a deletion of a single amino acid at the N-terminal. Further provided are chimeric polypeptides comprising the amino acid of SEQ ID NO:1 or an amino acid having 90% identity to SEQ ID NO:1 and one or more moieties that, for example, enhance delivery, sustain therapeutic action, or promote penetration of the blood brain barrier, or the like.

As used throughout, when Tβ-4 or SEQ ID NO:1 is referenced, it is understood that derivatives or modified versions thereof may be used.

By way of example, Tβ-4 can be isolated from biological sources, can be produced recombinantly, or can be produced using protein synthesis techniques. Tβ-4 is a commercially available product designated RGN-352 (Regenerx, Rockville, MD).

Those of skill in the art readily understand how to determine the percent identity of two proteins or nucleic acids, such as genes. For example, the identity can be calculated after aligning the two sequences so that the identity is at its highest level. Another way of calculating percent identity can be performed by published algorithms.

Optimal alignment of sequences for comparison may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. U.S.A. 85: 2444, by computerized implementations of these algorithms (GAP, BESTFIT, FASTA, and TFASTA in the Wisconsin Genetics Software Package, Genetics Computer Group, 575 Science Dr., Madison, WI), or by inspection. A sequence recited as having a particular percent identity to another sequence refers to sequences that have the recited identity as calculated by any one or more of the calculation methods described above. For example, a first sequence has 90 percent identity, as defined herein, to a second sequence if the first sequence is calculated to have 90 percent identity to the second sequence using a particular calculation method even if the first sequence does not have 90 percent identity to the second sequence as calculated by any of the other calculation methods.

The one or more chemotherapeutic agents that can be used include, but are not limited to, antineoplastic agents such as Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; 5-Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon α-2a; Interferon α-2b; Interferon α-n1; Interferon α-n3; Interferon (β-I a; Interferon γ-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin C; Mitosper; Mitotane; Mitoxantrone; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Temozolomide Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. By way of example, the chemotherapeutic agent is selected from the group consisting of doxorubicin, vincristine, cyclophosphamide, temozolomide and any combination thereof. However, any approved or experimental drug, either as monotherapies or as combinations, are optionally used in the present methods.

As used herein radiation refers to various forms of therapeutic radiation (e.g., external beam radiation, internal radiation therapy (via an implant), proton therapy). For children older than 3, radiation therapy is optionally directed to the entire brain and spine and is optionally followed by radiation therapy directed to the tumor. For children younger than 3, localized radiation therapy may be selected. Combination with the PI3K activator and a chemotherapeutic agent, however, may eliminate or reduce the need for radiation. Similarly, combination of the PI3K activator and radiation therapy may reduce the duration, frequency, or area of radiation. One of skill in the art can select the preferred radiation therapy.

In the methods provided herein, the PI3K activator and the one or more chemotherapeutic agents and/or radiation can be administered in series (e.g., with minutes, hours, or days of each other) or concurrently (i.e., simultaneously or nearly simultaneously). Current administrations can be as a single composition, through the same intravenous site or different intravenous sites, or by different mode administrations (e.g., one oral and one intravenously, subcutaneously, or intramuscularly)

As used herein the medulloblastoma to be treated is selected from MB subgroups including p53-mutated SHH (sonic hedgehog), MYC-p53, and p53-positive (wild-type or mutant) subgroups.

As used herein the term glioblastoma includes astrocytoma, grade IV and glioblastoma multiforme (GBM).

Optionally the methods of treatment as described herein further comprise determining the level of p53 in MB cells of the subject. Such a determination can be performed to determine whether the p13K activator is needed or to determine whether on-going treatment should be sustained or modified. When p53 levels are elevated (i.e., statistically higher than normal cells or higher than D283 cells or the like) then treatment with the p13K activator, in combination with one or more chemotherapeutic agents and/or radiation is initiated or continued. Various methods of determining levels of p53 are known in the art. By way of example, p53 levels can be determined by immunohistochemistry on a medulloblastoma cell biopsy of the subject.

Any of the methods provided herein can optionally further include surgery or administering radiation therapy to the subject.

Any of the methods provided herein can optionally include a biologic in addition to or instead of a small molecule chemotherapeutic. Examples of such biologics include but are not limited to Bevacizumab (AVASTIN®; Genentech, South San Francisco), pembrolizumab (KEYTRUDA®; Merck & Co., Inc., Whitehouse Station, NJ).

Provided herein are compositions comprising a PI3K activator and one or more chemotherapeutic agents. Also provided are kits comprising any combination of a PI3K activator, one or more chemotherapeutic agents, one or more containers, and one or more applicators (e.g., a syringe).

Throughout, treat, treating, and treatment refer to a method of reducing or delaying one or more effects or symptoms of medulloblastoma or glioblastoma. Treatment can also refer to a method of reducing the underlying pathology rather than just the symptoms. The effect of the administration to the subject can have the effect of, but is not limited to, reducing one or more symptoms (e.g., reduced pain, reduced size of the tumor, etc.) of the tumor, an increase in survival time, a decrease in metastasis, a decrease in time before metastasis, a reduction in the severity of the medulloblastoma or glioblastoma (e.g., reduced rate of growth of a tumor or rate of metastasis), the complete ablation of the medulloblastoma or glioblastoma or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between.

As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

In any of the methods provided herein, each of the PI3K activator and the chemotherapeutic agent and/or radiation can be administered in an effective amount. The term effective amount, as used throughout, is defined as any amount necessary to produce a desired physiologic response, i.e., treatment of medulloblastoma or glioblastoma. Effective amounts and schedules for administering a PI3K activator and one or more chemotherapeutic agents and/or radiation can be determined empirically and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, unwanted cell death, and the like. Generally, the dosage will vary with the type of PI3K activator, chemotherapeutic agent, and/or radiation, the level of synergism between the activator and the chemotherapeutic agent and/or radiation, the species, age, body weight, general health, sex and diet of the subject, the mode, time, and frequency of administration, rate of excretion, drug combination, and severity of the medulloblastoma or glioblastoma and can be determined by one of skill in the art. The dosage can be adjusted by the individual physician in the event of any contraindications.

Exemplary dosage amounts for administration of a PI3K activator like Tβ-4 include doses of about 0.5-2000 mg for each administration, which may be administered with the same frequency as the one or more chemotherapeutic agents and/or radiation or may be administered with greater or less frequency than the one or more chemotherapeutic agents and/or radiation. Thus, doses of about 1-1000 mg, 10-100 mg, and any amount in between may be used. One of skill in the art would adjust the dosage as described below based on specific characteristics of the inhibitor and the subject receiving it.

Any of the PI3K activators described herein can be provided in a pharmaceutical composition. These include, for example, a pharmaceutical composition comprising a therapeutically effective amount of one or more PI3K activators and a pharmaceutical carrier, optionally further comprising one or more chemotherapeutic agents.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012).

Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, New Jersey), polyethylene glycol (PEG), and PLURONICS™ (BASF; Florham Park, NJ).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

The compositions are administered in a number of ways depending on whether local or systemic treatment is desired, and on the area to be treated. The compositions are administered via any of several routes of administration, including orally, parenterally, intravenously, intraperitoneally, intramuscularly, subcutaneously, intrarectally, intracavity, transdermally, intraventricularly, or transvertebrally (i.e., into the cerebrospinal fluid). Pharmaceutical compositions can also be delivered locally to the area in need of treatment, for example by local injection (e.g., intracerebrally, into other brain regions, or into the spinal cord). Effective doses for any of the administration methods described herein can be extrapolated from dose-response curves derived from in vitro or animal model test systems.

The examples below are intended to further illustrate certain aspects of the methods and compositions described herein, and are not intended to limit the scope of the claims.

Examples

Example 1: In Vitro Analysis

Figure 2A:
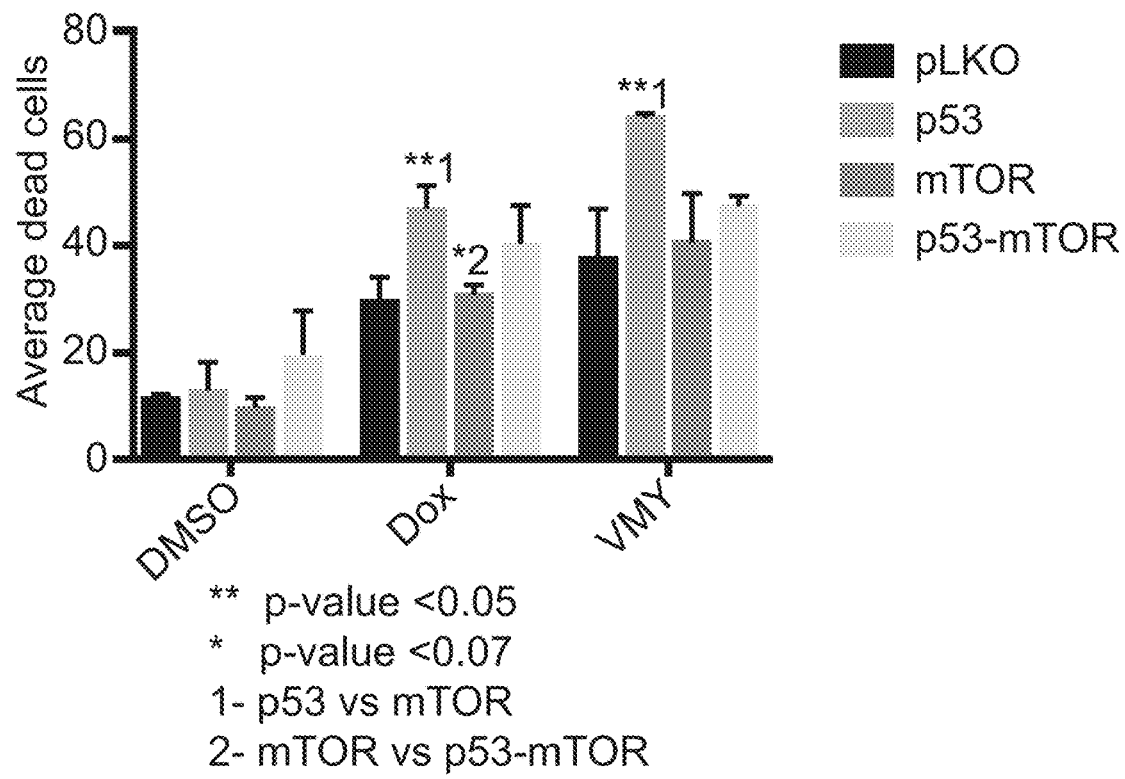
FIGS. 2A, 2B and 2C show the effect of silencing of p53 and mTOR in D556 cells.
Figure 2B:
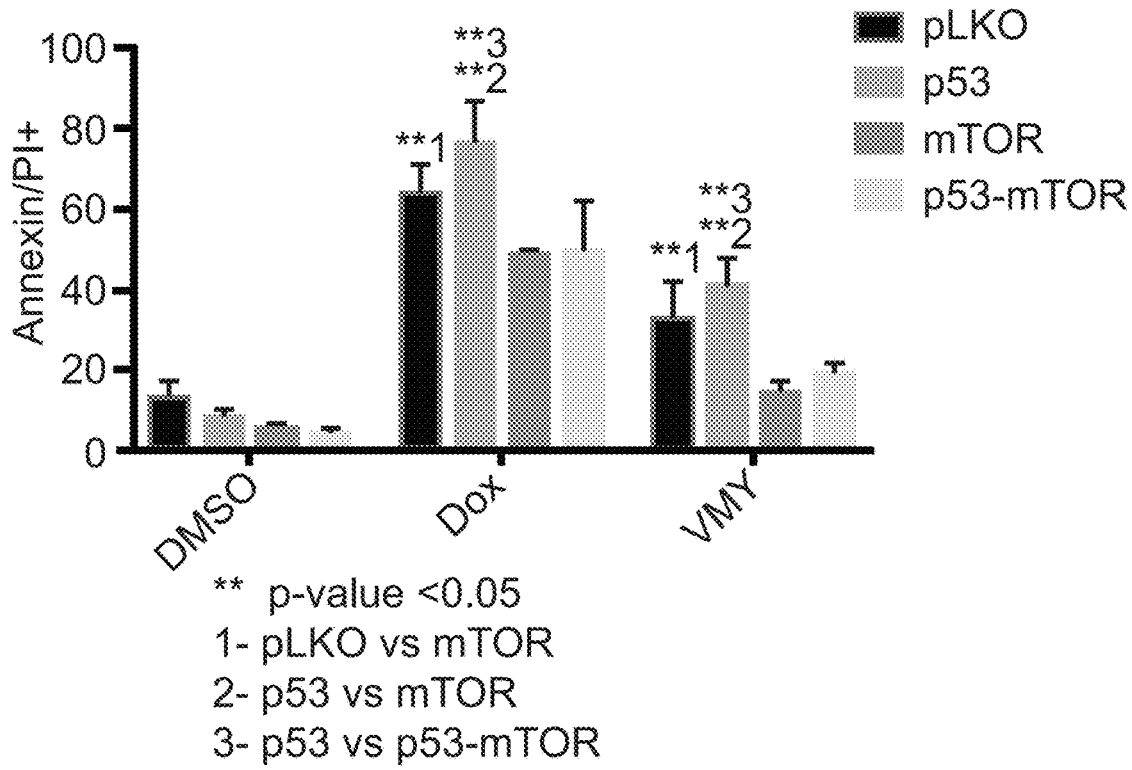
Figure 2C:
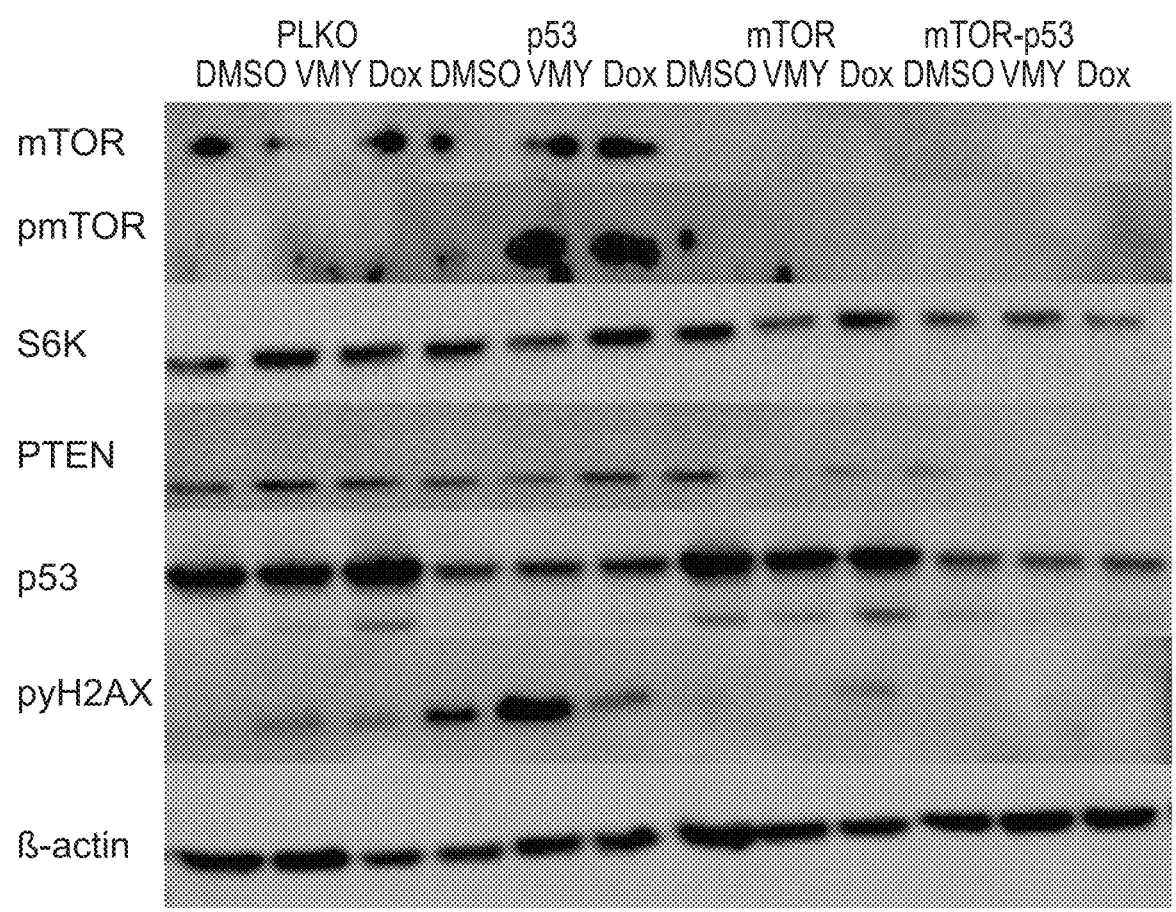

Transcriptomic profiling of p53-suppressed D556 cells revealed that enhanced chemosensitivity was associated with the activation of mTOR and PI3K, among other genes. D556 cells were infected with either p53 shRNA or control pLKO lentivirus and Western blotting was performed to show the effect of p53 inhibition on pmTOR. Treatment of the cells with either doxorubicin or VMP showed induction of pmTOR in cells infected with p53 shRNA as compared to pmTOR levels in cells infected with the control pLKO lentivirus. See FIG. 1.

shRNA knockdown of mTOR rescued the D556 cells from the effects of p53 loss, restoring chemoresistance to vincristine and doxorubicin. The proportion of cells undergoing apoptotic cell death as a result of infection with p53 shRNA, control pLKO, mTOR and both p53 and mTOR lentivirus in D556 cells treated for 18 hrs with DMSO, VMY (30 uM) or doxorubicin (1 uM) was assessed using trypan blue (FIG. 2A) and annexin V and propidium iodide (PI) staining (FIG. 2B) and measured by flow cytometry. Data were determined as the percent change in staining versus pLKO-control infected cells. Immunoblotting was performed for the proteins shown in FIG. 2C.

Figure 3A:
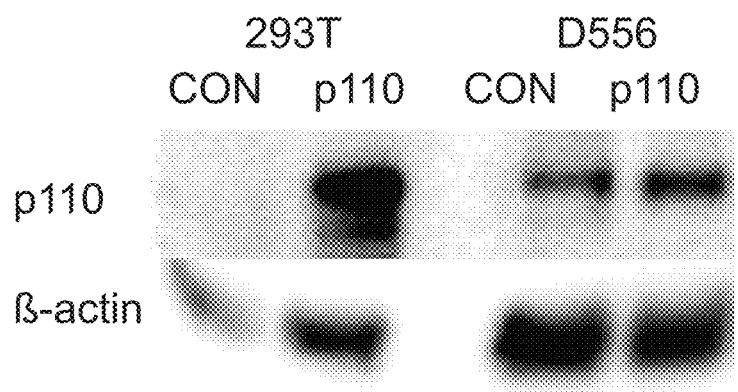
FIGS. 3A, 3B, 3C, 3D, and 3E show the effects of over expression of p110-caax on D556 and D283 cell survival. D556 cells were transformed with p110 or control plasmid, and Western blots for p110 and $\beta$-actin were run (FIG. 3A). The effects of overexpression of p110 on cell viability were determined via Trypan blue assay on D283 cells (FIG. 3B, upper right panel) and D556 cells (FIG. 3C, lower left panel) showing Trypan blue assay results; lower middle panel showing). Cell viability for D556 cells was also measured by propidium iodide (PI) staining and measured by flow cytometry (FIG. 3D, lower middle panel)). Reversal of chemosensitivity induced by p110 overexpression is shown when an inhibitor of mTOR/AKT signaling (Rad001/Everolimus) is added (FIG. 3E)
Figure 3B:
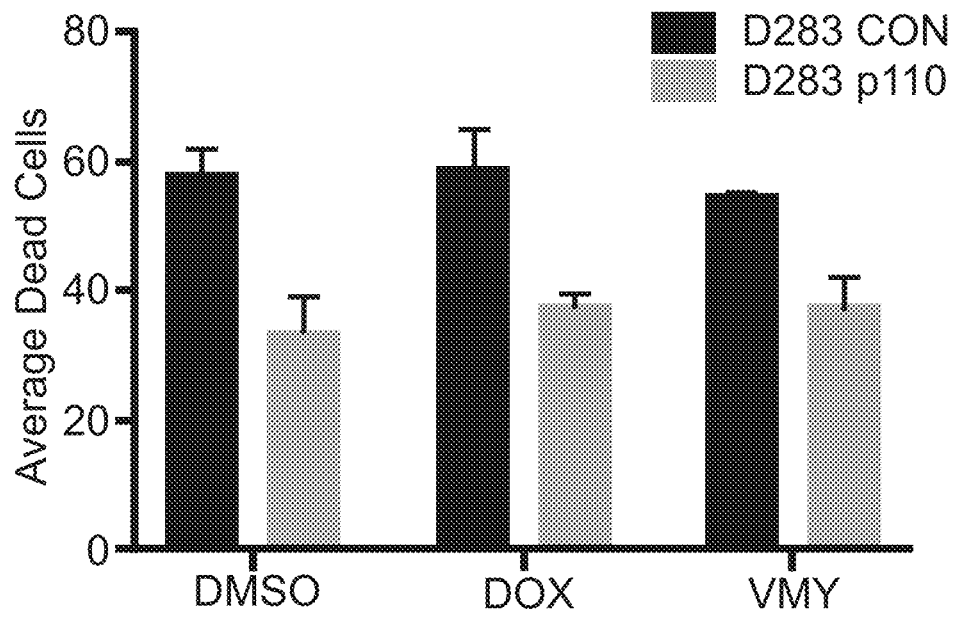
Figure 3C:
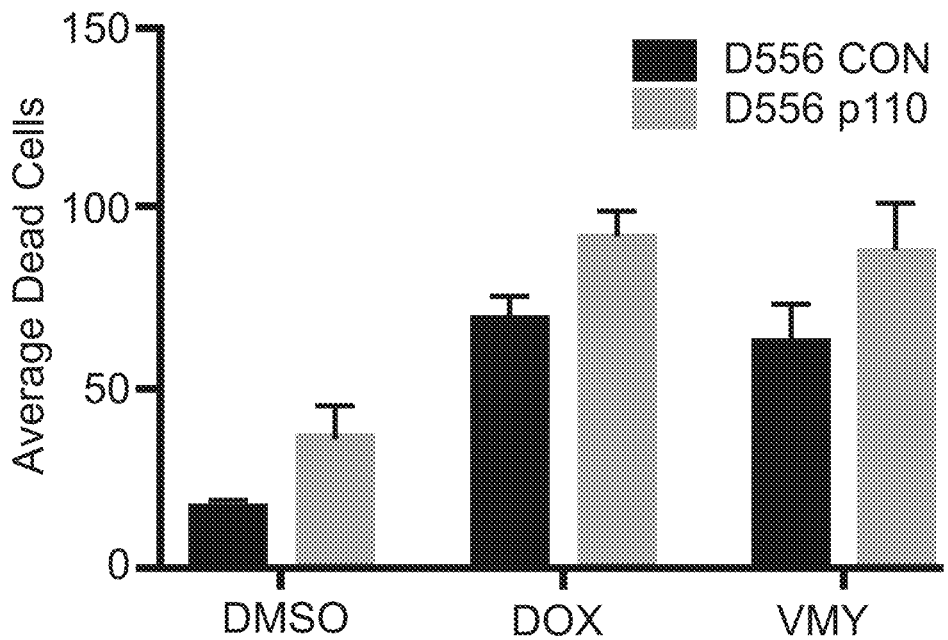
Figure 3D:
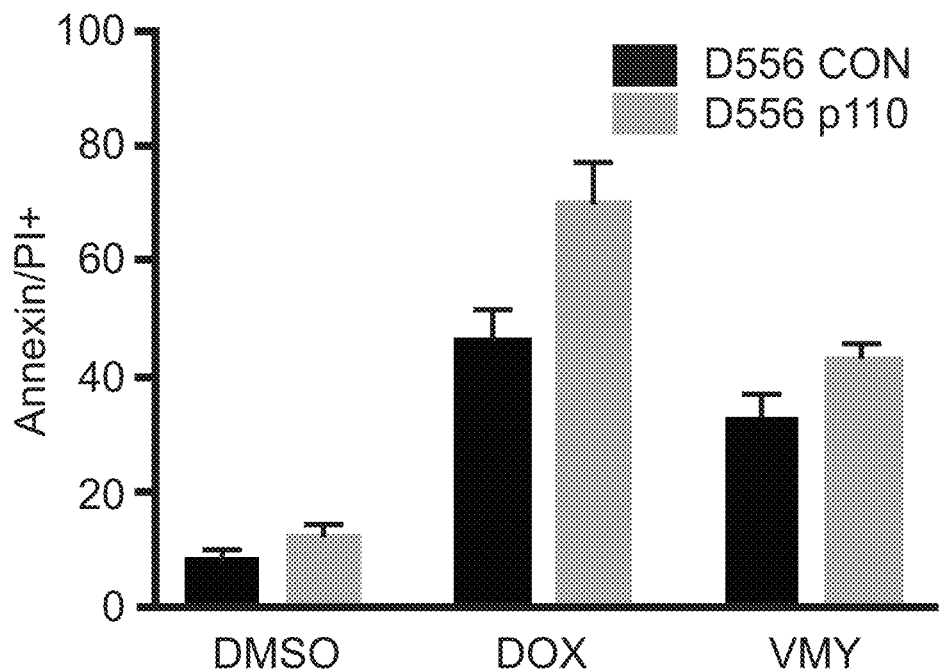
Figure 3E:
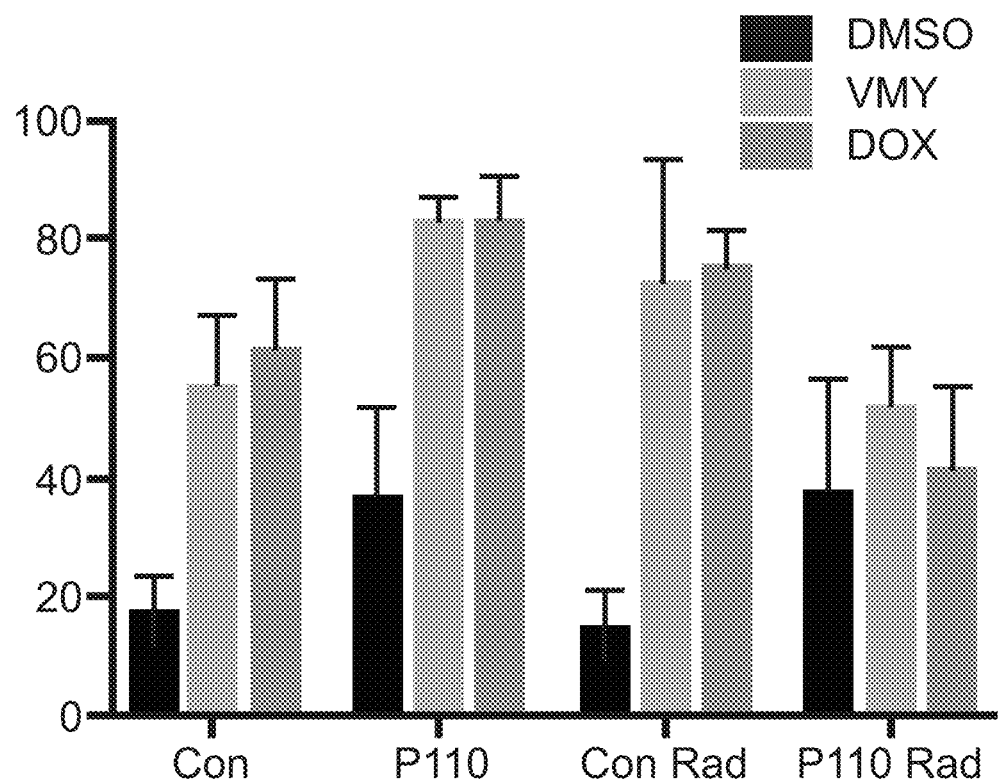

Conversely, the overexpression of p110a to induce PI3-kinase-dependent signaling, resulted in a twofold increase in drug sensitivity in D556 cells while D283 cells were approximately twofold more chemoresistant. D556 cells were transformed with p110 or control plasmid and Western blots for p110 and β-actin were run (FIG. 3A). The effects of overexpression of p110 on cell viability were determined via Trypan blue assay on D283 cells (FIG. 3B) and D556 cells (FIG. 3C). Cell viability for D556 cells was also measured by propidium iodide (PI) staining and measured by flow cytometry (FIG. 3D). An inhibitor of p110 (Rad001/Everolimus) reversed the chemosensitivity induced by p110 (FIG. 3E)

Figure 4A:
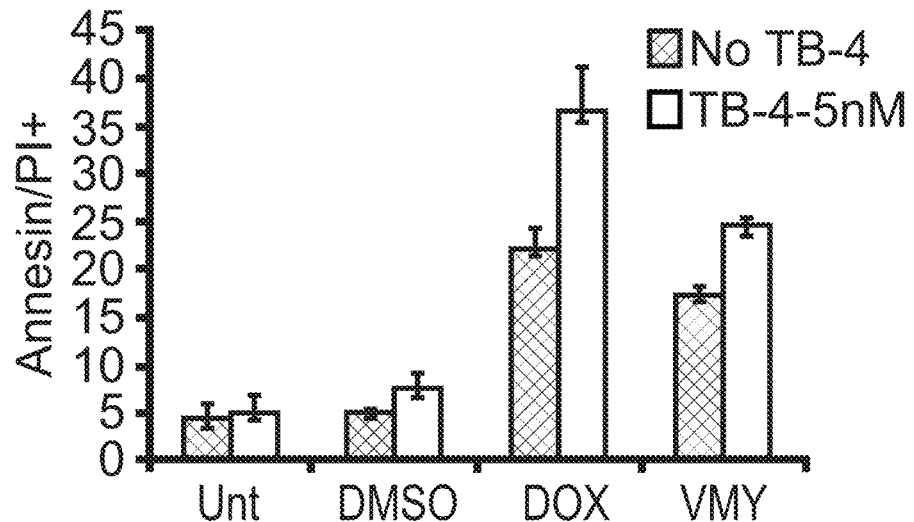
FIGS. 4A, 4B, and 4C show the effects of thymosin beta-4 (T$\beta$-4) on D556 and D283 cell survival. For cell viability assays, D556 cells (FIG. 4A) and D283 cells (FIG. 4B) were treated with DMSO, doxorubicin, or VMY in the presence or absence of T$\beta$-4, and cell viability as measured using propidium iodide (PI) staining with flow cytometry. Control cells were untreated.
Figure 4B:
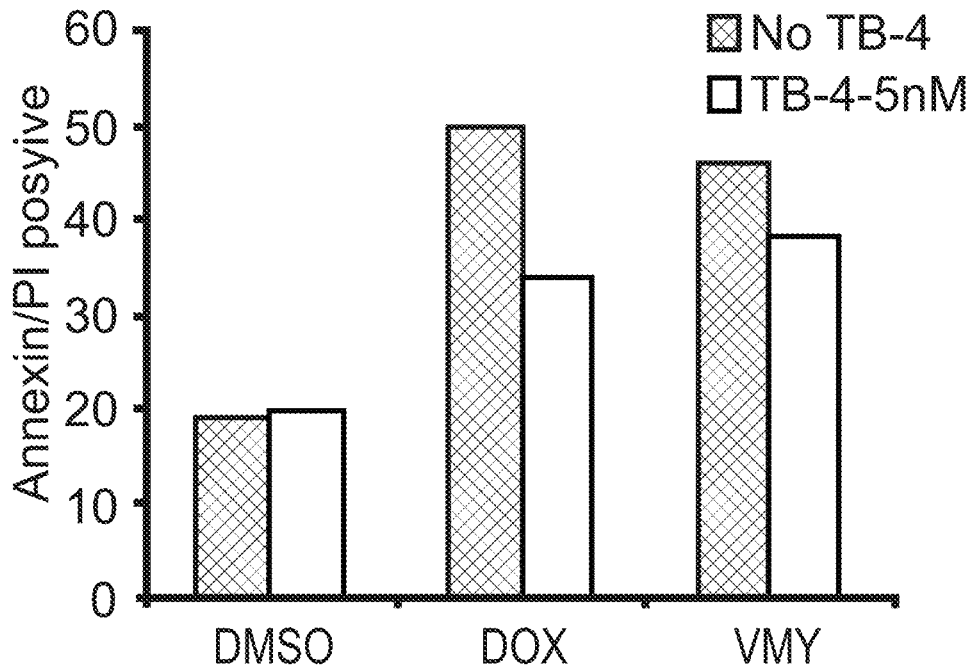
Figure 4C:
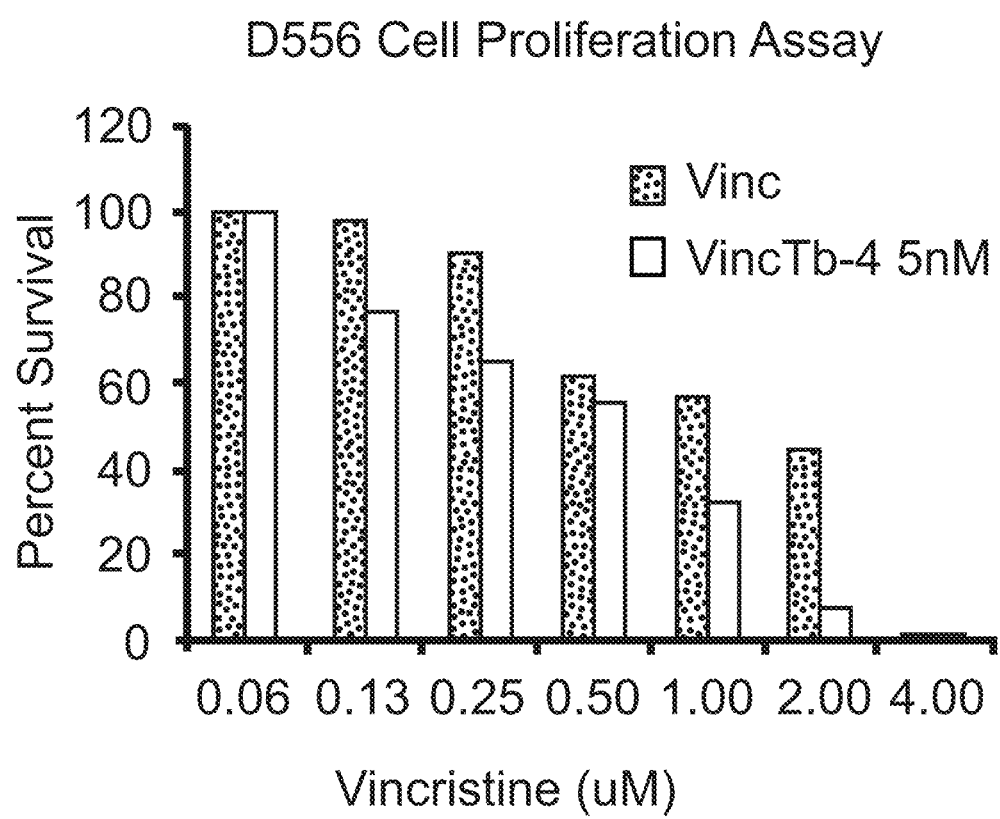
Figure 5A:
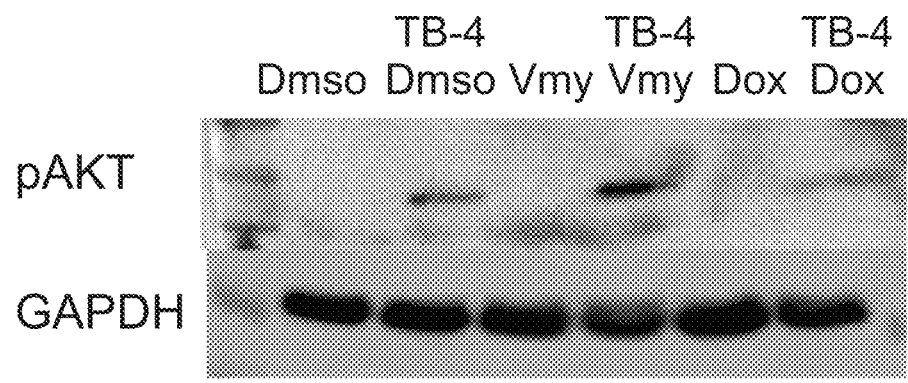
FIGS. 5A, 5B, 5C and 5D are Western blots showing that T$\beta$-4 treatment of D556 cells induces expression of Akt, PP2A ($\alpha$ and c subunits), PARP, and RIP1.
Figure 5B:
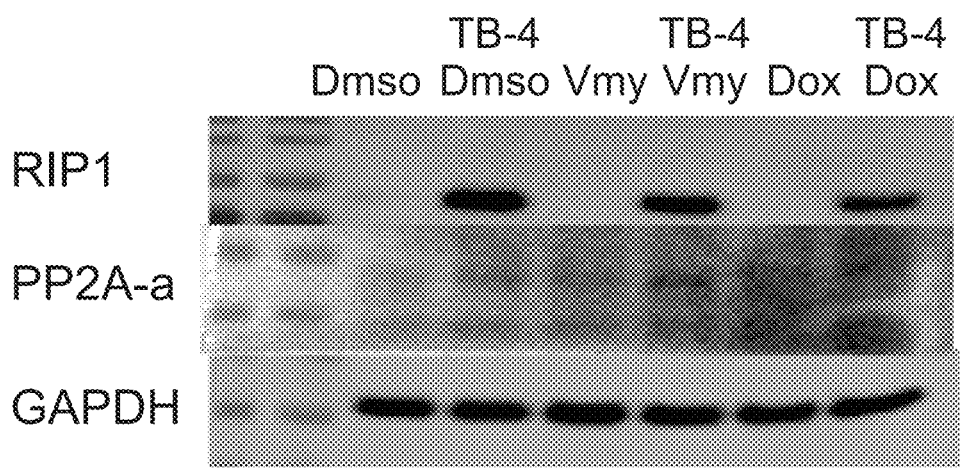
Figure 5C:
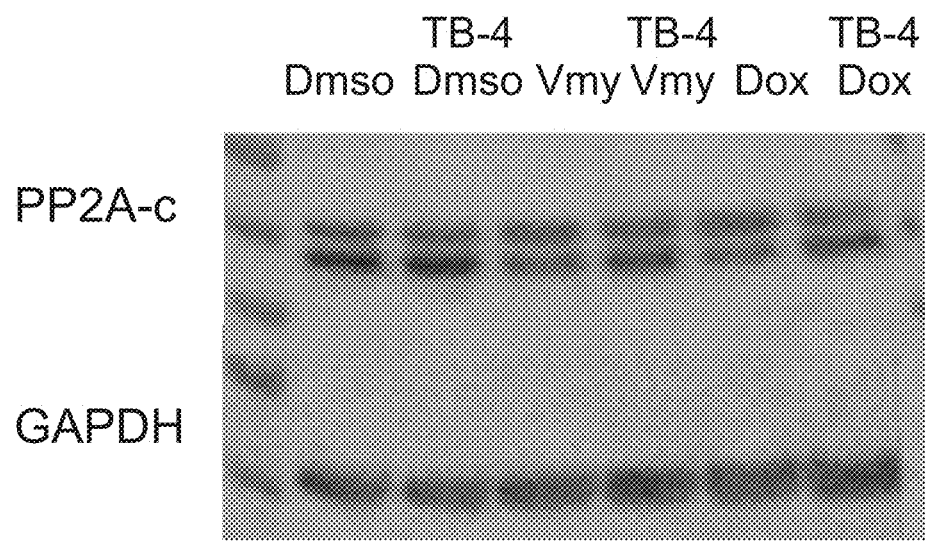
Figure 5D:
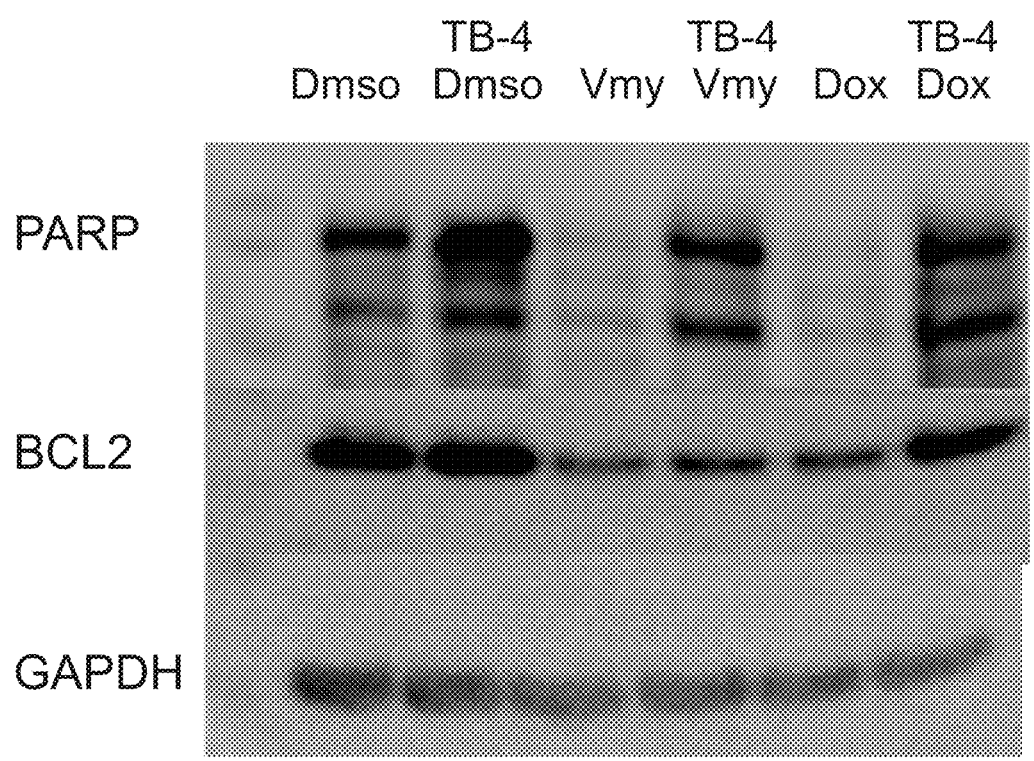

The effect of Tβ-4 was evaluated using a cell viability assay for D556 and D283 cells. D556 and D283 cells were treated with 5 nM Tβ-4 and either doxorubicin or VMY. Viability of D556 cells (FIG. 4A) and of D283 cells (FIG. 4B) was measured using propidium iodide (PI) staining with flow cytometry. A dose response curve was performed for D556 cells treated with vincristine alone or vincristine plus Tβ-4 using a cellular proliferation assay kit wst-1 (FIG. 4C).

To further assess the mechanism of effect of Tβ-4 treatment of D556 cells, Western blot were performed. Treatment with Tβ-4 induces Akt, PP2A (α and c subunit), PARP and RIP1 in D556 cells.

Figure 6A:
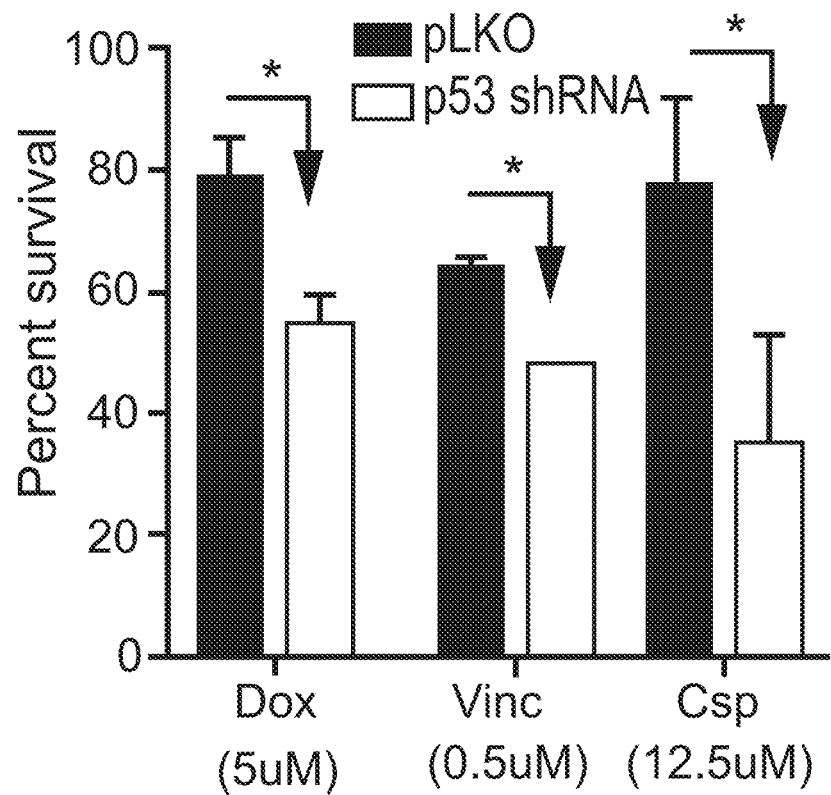
FIG. 6A shows cell survival of D556 cells following p53 knockdown and treatment with doxorubicin (dox), vincristine (vinc) and cisplatin (csp). Comparative sensitivities of D556 cells treated with cisplatin (FIG. 6B) or vincristine (FIG. 6C) were tested at the concentrations shown and in the presence or absence of thymosin $\beta$-4 (5 nM). * p<0.05, N>3 separate experiments.
Figure 6B:
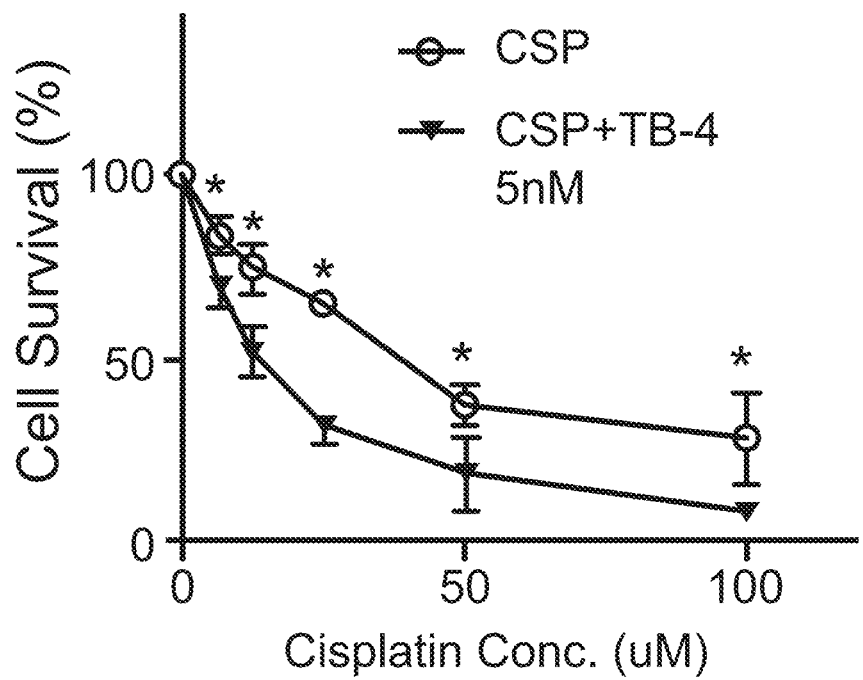
Figure 6C:
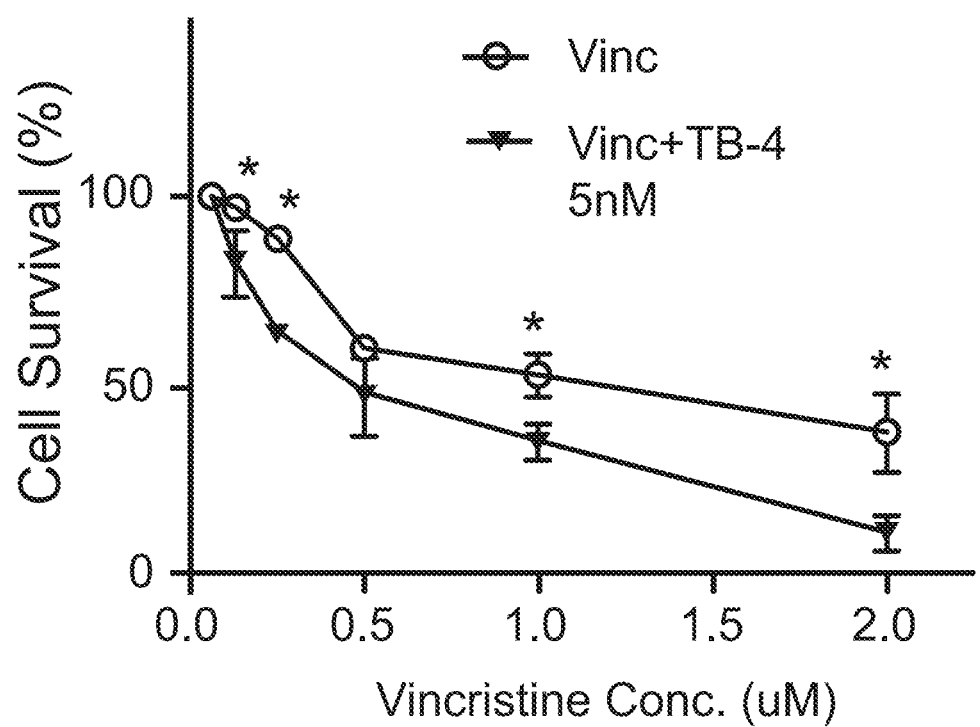

For chemosensitivity testing, the effects of p53 knockdown on cell survival of D556 cells treated with doxorubicin (dox), vincristine (vinc) and cisplatin (csp) was further assessed. As shown in FIG. 6A, D556 cells infected with p53 shRNA showed a lower percentage of cell survival following treatment (18 hours) with doxorubicin, vincristine, or cisplatin, as compared to cells infected with a control pLKO lentivirus. D556 cells treated with cisplatin (FIG. 6B) or vincristine (FIG. 6C) at the concentrations shown in the presence of Tβ-4 (5 nM) showed significantly more sensitivity to both cisplatin and vincristine that D556 cells in the absence of Tβ-4. As shown in FIG. 6B and FIG. 6C.

Example 2: In Vivo Orthotopic Mouse Model of MB

D556 and D283 cells are stereotactically implanted into the brains of immunocompromised athymic nude mice. For orthotopic tumor implantation, male and female NCI athymic nude mice are anesthetized using 1-3% isoflurane in oxygen. An incision is made in the midline of the scalp over the cerebellum, and a small hole 1 mm lateral to the midline will be made with an 18 G needle. A 24 G Hamilton syringe, loaded with $5 \times 10^5$ MB cells in tissue culture media mounted on a micromanipulator, is used to implant the cells at a 30° angle to the surface of the cerebellum, at a depth of 1 mm over the course of 1-2 min. The needle is left in place for another 2 min to avoid reflux. 0.25% (2.5 mg/mL) bupivacaine (Hospira) is applied along the incision for postoperative analgesia, and the skin is closed with glue.

The effects of the first-line MB chemotherapeutic agents, vincristine or cisplatin, alone and in combination with Tβ-4, are assessed by longitudinal magnetic resonance imaging (MRI). Specifically, tumor progression and drug responses are quantified by MRI volumetry and the effects on tumor metabolism will be defined by MR-spectroscopy (MRS). For MRI, anesthetized mice will be imaged in the PIRL's Bruker Biospec 7T magnet using a custom stereotaxic holder with built-in biometric monitoring and engineered to fit Bruker imaging coils. For tumor volumetry, T2-weighted RARE (rapid acquisition with relaxation enhancement) imaging is performed as previously described (Beauchamp et al. (2011) J Clin Invest 121, 148-160; Sirajuddin et al. (2012) Cell Cycle 11, 3801-3809. For MRS, single voxel proton MRS is performed using PRESS (Position Resolved Spectroscopy Sequence), essentially as previously described (Sirajuddin et al.). The voxel is located entirely in tumor areas avoiding contamination from normal brain tissue using the RARE anatomical image.

Quantification of neurochemicals is performed using the Bruker TOPSPIN software. Animals are randomized for treatment when their MB masses reach 100 mm³ or greater. Treatments continue until a 20% difference in overall tumor size between drug versus drug plus Tβ-4 is detected or until the masses grow over 1 cm³, and time to death is assessed by Kaplan-Meier survival analysis. Power analyses: Approximately ten tumors per treatment group allows detection of differences of 20% in tumor growth between drug vs drug+Tβ-4, with an alpha=0.05 and power=0.80. Based on an approximate 80% success rate in inducing human MB in nude mice, twelve mice per treatment are needed. There are five treatment groups (vincristine, cisplatin, Tβ-4, vincristine+Tβ-4, cisplatin+Tβ-4 and vehicle alone). Two Group 3 MB cell lines are tested, that is, D556 cells which were Tβ-4 sensitive and the D286 cells which were Tβ-4 insensitive. Additional cell lines, such as DAOY, are also tested.

Example 3: Ex Vivo Analyses

The final MRI informs tumor location and size. The tumors are then excised and used for RNA isolation, protein extraction and for histopathological analysis. Western blotting and immunohistochemistry (IHC) are performed as previously described (Tian et al. (2014) Comp Biol and Bioinformatics 11, 1009-1019; Sirajuddin et al.; Rodriguez et al. (2009) Am J Pathol 174, 2051-2060; 11, 13). Expression levels of Myc, PP2a and RIPK1. TUNEL assays are run to assess necroptosis in the tumors as previously described (Sirajuddin et al.).

All in vivo and ex vivo effects of drug versus drug+Tβ-4 on tumors will be defined using the 2-tailed Student's t test or the 1-way analysis of variance (ANOVA) as previously described (Tian et al.).

All references cited herein are hereby incorporated by reference in their entireties for the cited teachings therein.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the composition and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term comprising and variations thereof as used herein is used synonymously with the term including and variations thereof and are open, non-limiting terms. Although the terms comprising and including have been used herein to describe various embodiments, the terms consisting essentially of and consisting of can be used in place of comprising and including to provide for more specific embodiments of the invention and are also disclosed.

The invention claimed is:

1. A method of treating a medulloblastoma subgroup selected from the group consisting of p53-mutated sonic hedgehog subgroup, MYC-p53 subgroup, and p53-positive subgroup in a subject comprising administering to the subject a chemotherapeutic agent and a PI3K activator.

2. The method of claim 1, wherein the pI3K activator is thymosin β-4 or a derivative thereof.

3. The method of claim 1, wherein the medulloblastoma comprises cells with elevated p53 levels.

4. The method of claim 1, wherein the chemotherapeutic agent is selected from the group consisting of doxorubicin, vincristine, cyclophosphamide, temozolomide, and any combination thereof.

5. The method of claim 1, wherein the PI3K activator reduces the effect of the chemotherapeutic agent on normal cells and enhances the effect of the chemotherapeutic agent on medulloblastoma cells.

6. The method of claim 1, further comprising determining the level of p53 in medulloblastoma cells of the subject.

7. The method of claim 1, wherein the PI3K activator crosses the blood brain barrier.

8. The method of claim 1, wherein the PI3K activator is a peptide having at least 90% identity to SEQ ID NO:1.

9. The method of claim 1, wherein the PI3K activator is a peptide having SEQ ID NO:1.

10. The method of claim 1, wherein the chemotherapeutic agent is doxorubicin.

11. The method of claim 1, further comprising administering radiation therapy to the subject.

12. The method of claim 1, further comprising administering a biologic to the subject.

13. The method of claim 12, wherein the biologic is bevacizumab or pembrolizumab.

14. The method of claim 1, wherein the PI3K activator is administered in a dose of 0.5 to 2000 mg for each administration.

15. The method of claim 14, wherein the PI3K activator is administered in a dose of 1 to 1000 mg.

16. The method of claim 14, wherein the PI3K activator is administered in a dose of 10 to 100 mg.

17. The method of claim 1, wherein the PI3K activator is administered by injection.

18. The method of claim 1, wherein the PI3K activator is administered orally.

19. The method of claim 1, wherein the chemotherapeutic agent is administered orally or intravenously.

* * * * *